US009383298B2

(12) United States Patent
O'Caoimh et al.

(10) Patent No.: US 9,383,298 B2
(45) Date of Patent: Jul. 5, 2016

(54) METHOD FOR PREPARING A SAMPLE FOR ANALYSIS

(71) Applicants: Ronan Patrick O'Caoimh, Delgany (IE); James Walsh, Monkstown (IE); Brendan Kevin Farrell, Glenealy (IE); Rory Peter Nealon, Blackrock (IE); Josef Georg Hubert Wiehe, Hoexter (DE)

(72) Inventors: Ronan Patrick O'Caoimh, Delgany (IE); James Walsh, Monkstown (IE); Brendan Kevin Farrell, Glenealy (IE); Rory Peter Nealon, Blackrock (IE); Josef Georg Hubert Wiehe, Hoexter (DE)

(73) Assignee: Tcoag Ireland Limited, Dublin (IE)

( * ) Notice: Subject to any disclaimer, the term of this patent is extended or adjusted under 35 U.S.C. 154(b) by 614 days.

(21) Appl. No.: 13/835,564

(22) Filed: Mar. 15, 2013

(65) Prior Publication Data
US 2013/0210161 A1 Aug. 15, 2013

Related U.S. Application Data

(62) Division of application No. 12/517,305, filed as application No. PCT/IE2007/000120 on Dec. 5, 2007, now Pat. No. 8,420,030.

(30) Foreign Application Priority Data

Dec. 5, 2006 (IE) .................................... S2006/0872

(51) Int. Cl.
*G01N 1/38* (2006.01)
*G01N 11/10* (2006.01)
(Continued)

(52) U.S. Cl.
CPC ................ *G01N 1/38* (2013.01); *B01L 3/5085* (2013.01); *G01N 11/10* (2013.01); *G01N 11/14* (2013.01); *G01N 11/16* (2013.01);
(Continued)

(58) Field of Classification Search
CPC ......... G01N 1/38; G01N 11/10; G01N 11/14; G01N 11/16; G01N 2011/147; B01L 3/5085; B01L 2300/0627; B01L 2300/0654; B01L 2300/0851; B01L 2300/0829; Y10T 436/2575
See application file for complete search history.

(56) References Cited

U.S. PATENT DOCUMENTS

| 3,967,934 | A | * | 7/1976 | Seitz | G01N 33/4905 422/73 |
| 4,478,094 | A | * | 10/1984 | Salomaa | G01N 1/38 422/552 |
| 4,918,984 | A | * | 4/1990 | Martinoli | B01F 11/0082 73/64.43 |
| 5,125,748 | A | * | 6/1992 | Bjornson | G01N 21/253 356/414 |

(Continued)

FOREIGN PATENT DOCUMENTS

BE 895652 A1 5/1983
EP 1255115 A2 11/2002

OTHER PUBLICATIONS

Beyer, Uwe et al. "Compensation of temperature and concanavalin A concentration effects for glucose determination by the viscometric affinity assay." Biotechnol. Prog. (2000) 16 1119-1123.*

*Primary Examiner* — Christopher A Hixson
(74) *Attorney, Agent, or Firm* — Sughrue Mion, PLLC

(57) ABSTRACT

A well plate (1) for holding samples of a bodily fluid during analysis thereof, typically in an analytical apparatus, includes a plate (2) having a plurality of first wells (3) extending downwardly therefrom for holding a sample during optical analysis of the sample, and a plurality of second wells (4) for holding samples during mechanical analysis of the samples. A plurality of holding wells (8) are provided for initially receiving and holding samples of the bodily fluid to be analysed so that samples of relatively accurate size can be pipetted from the holding wells (8) to the first and second wells (3,4).

15 Claims, 2 Drawing Sheets

(51) Int. Cl.
*G01N 11/14* (2006.01)
*G01N 11/16* (2006.01)
*B01L 3/00* (2006.01)
*G01N 21/03* (2006.01)

(52) U.S. Cl.
CPC . *B01L 2300/0627* (2013.01); *B01L 2300/0654* (2013.01); *B01L 2300/0829* (2013.01); *B01L 2300/0851* (2013.01); *G01N 2011/147* (2013.01); *G01N 2021/0378* (2013.01); *Y10T 436/2575* (2015.01)

(56) References Cited

U.S. PATENT DOCUMENTS

| | | |
|---|---|---|
| 5,359,184 A | 10/1994 | Froehlich |
| 6,143,250 A | 11/2000 | Tajima |
| 2002/0094578 A1* | 7/2002 | Kowallis ............... B01L 3/5085 436/43 |
| 2002/0141905 A1 | 10/2002 | Sha |
| 2005/0236317 A1 | 10/2005 | Desilets et al. |
| 2006/0008387 A1 | 1/2006 | Tansey |

* cited by examiner

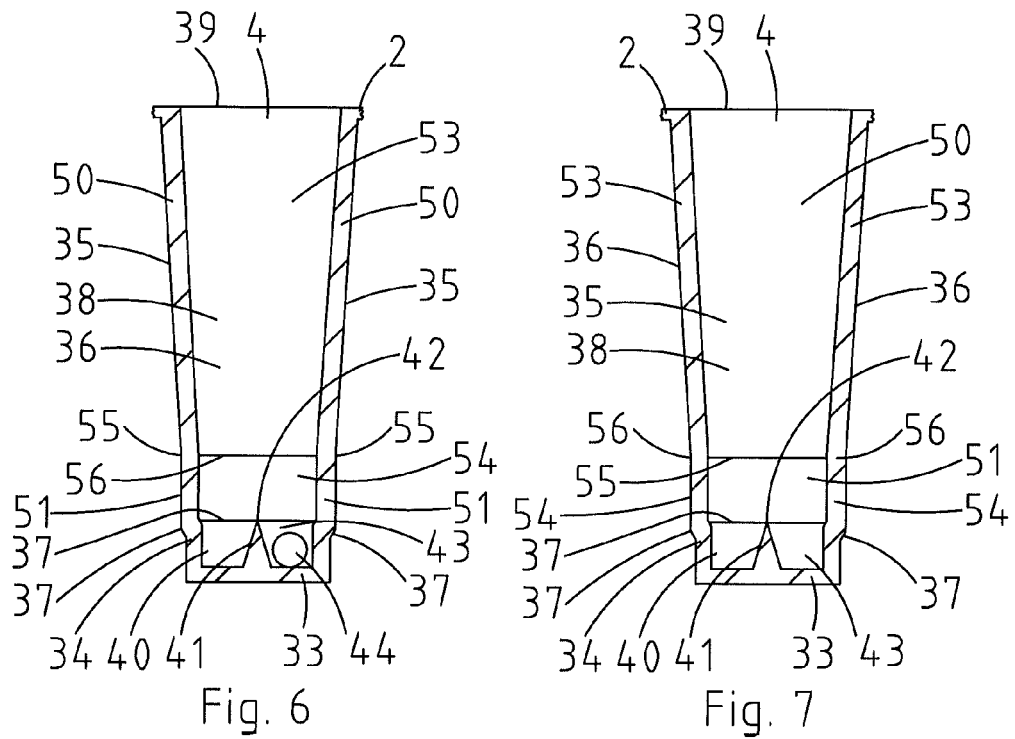
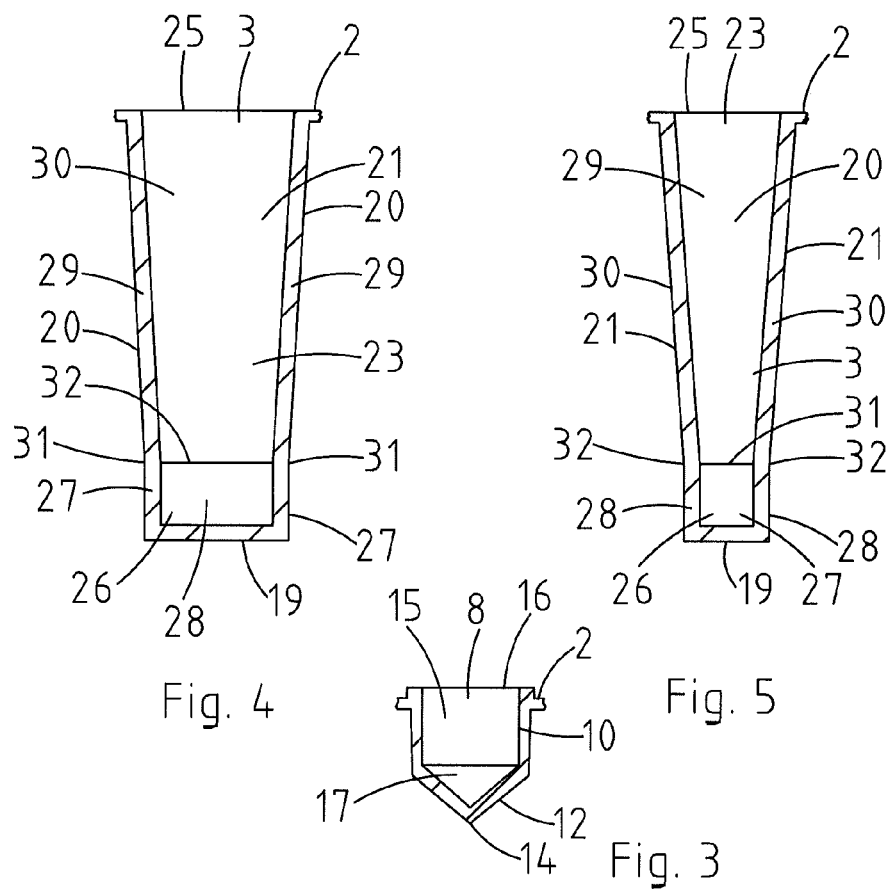

METHOD FOR PREPARING A SAMPLE FOR ANALYSIS

CROSS-REFERENCE TO RELATED APPLICATIONS

This application is a divisional of U.S. application Ser. No. 12/517,305 filed Mar. 29, 2010, which application is a 371 of PCT International Application No. PCT/IE2007/0000120 filed on Dec. 5, 2007, which claims benefit of Irish Patent Application No. S2006/0872 filed Dec. 5, 2006, the disclosures of which are incorporated herein by reference in their entirety.

BACKGROUND OF THE INVENTION

The present invention relates to a well plate for holding a sample during analysis thereof, and in particular, though not limited to a well plate for holding a liquid sample such as bodily fluid during analysis thereof. The invention also relates to a method for preparing a sample for analysis, and in particular, though not limited to a method for preparing a sample of bodily fluid for analysis.

Well plates for holding samples, and in particular, liquid samples, such as bodily fluids, for example, blood, blood plasma, urine and other such bodily fluids during analysis in analytical apparatus are known. Typically, such well plates comprise a plate having a plurality of wells located therein in which the samples to be analysed are placed, typically, by pipetting into the wells from a vial or vials containing the samples. Such well plates may comprise an elongated strip plate which may be of flexible, semi-rigid or rigid material having a plurality of wells located therein arranged in a single column extending longitudinally along the strip plate. Alternatively, the well plate may comprise a plate having the wells arranged in a matrix formed by a plurality of rows and columns of the wells. Typically, the well plate is adapted for use in a particular analytical apparatus in which the samples are to be analysed.

The wells may be of a type which are adapted for optical analysis whereby light is directed at or through the sample in the well, and the spectrum of the light reflected from or transmitted through the sample is analysed in order to determine a characteristic of the sample, for example, a characteristic which would indicate the state of health of a subject from whom the sample of bodily fluid was obtained.

Alternatively, the wells may be of the type which are adapted for carrying out a mechanical analysis of a sample. Such mechanical analyses, in general, are carried out by determining the viscosity of the sample. Many mechanical methods are known for use in analytical apparatus for determining sample viscosity. A particularly common method is based on determining the speed at which a ball travels through the liquid sample. Typically, the ball is of steel or another suitable magnetically sensitive material, and is energised to move through the sample by applying a magnetic field externally of the well. The viscosity of the liquid sample is determined by comparing the speed with which the ball moves through the sample with the strength of the energising magnetic field.

Such known well plates are adequate for carrying out optical and mechanical analysis where the accuracy of the sample size which is placed in the well is not critical. However, where the sample size is critical, such well plates are unsuitable. This is as a result of the fact that, in general, the sample is transferred to a well in the well plate by pipetting from a vial containing the sample. Such vials typically are closed by a stopper of a rubber or rubber type plastics material. Pipetting of the sample from the vial to the well in the well plate is carried out by piercing the stopper of the vial with a pointed cannula which is then inserted through the stopper into the vial, and a volume of the sample is withdrawn into the cannula. However, due to the fact that the vial is closed by the stopper during pipetting of the sample, the pressure within the vial may vary above or below atmospheric pressure as a result of temperature, and indeed, the mere insertion of the stopper in the vial when closing the vial may be sufficient to increase the pressure within the vial above atmospheric pressure. Accordingly, variation in pressure within the container from which the sample is being pipetted results in a variation of the sample size withdrawn from the vial by pipetting. This is unsatisfactory where the sample size is critical.

Another problem with well plates known heretofore is that in general, the wells are unsuitable for mixing a sample with a reagent.

There is therefore a need for a well plate for holding a sample of material during analysis which addresses at least some of the problems of known well plates, and there is also a need for a method for preparing a sample for analysis using a well plate.

The present invention is directed towards providing such a well plate and such a method.

SUMMARY OF THE INVENTION

According to the invention there is provided a well plate for holding a sample during analysis thereof, the well plate comprising a plate, at least one analysis well located in the plate for holding the sample during analysis, and at least one holding well located in the plate for receiving the sample prior to transfer to the analysis well.

Preferably, each holding well is located adjacent at least one of the analysis wells.

In one embodiment of the invention each holding well defines a hollow interior region extending downwardly from an upwardly facing open mouth for accommodating the sample into the hollow interior region. Preferably, the hollow interior region defined by each holding well terminates in a downwardly tapering portion.

In another embodiment of the invention the downwardly tapering portion of the hollow interior region defined by each holding well is of frustoconical shape. Alternatively, the downwardly tapering portion of the hollow interior region defined by each holding well is of conical shape.

In another embodiment of the invention a portion of the hollow interior region intermediate the open mouth and the downwardly tapering portion of each holding well is of cylindrical shape.

Advantageously, the open mouth of each holding well is located adjacent the plate.

Preferably, each holding well extends downwardly from the plate. Advantageously, each holding well is located between two adjacent analysis wells.

In one embodiment of the invention at least one of the analysis wells is provided by a first well adapted for holding a sample during an optical analysis thereof. Preferably, each first well defines a hollow interior region extending downwardly from an open mouth for accommodating the sample into the hollow interior region.

Advantageously, the hollow interior region defined by each first well terminates in a sample accommodating portion for holding the sample during analysis thereof comprising a planar base and an upwardly extending side wall. Ideally, the planar base of each first well is of rectangular shape.

In one embodiment of the invention the sample accommodating portion of each first well comprises a pair of spaced apart side walls extending upwardly from the base thereof, joined by a pair of spaced apart end walls extending upwardly from the base.

Preferably, the side walls of the sample accommodating portion of each first well extend parallel to each other, and the end walls of the sample accommodating portion of each first well extend parallel to each other. Advantageously, the hollow interior region defined by each first well tapers downwardly from the open mouth thereof to the sample accommodating portion. Ideally, the tapering portion of the hollow interior region of each first well is of rectangular transverse cross-section.

In one embodiment of the invention the tapering portion of the hollow interior region of each first well is formed by a pair of spaced apart side walls diverging upwardly from each other from the sample accommodating portion, joined by a pair of spaced apart end walls diverging upwardly from each other from the sample accommodating portion.

Advantageously, the open mouth of each first well is located adjacent the plate.

Preferably, each first well extends downwardly from the plate.

In another embodiment of the invention at least one of the analysis wells is provided by a second well adapted for holding the sample during a mechanical analysis thereof. Preferably, each second well defines a hollow interior region extending downwardly from an open mouth for accommodating the sample into the hollow interior region. Advantageously, the hollow interior region defined by each second well terminates in a sample accommodating portion for holding the sample during analysis thereof. Ideally, the hollow interior region defined by each second well tapers downwardly from the open mouth thereof to the sample accommodating portion.

In one embodiment of the invention the tapering portion of the hollow interior region of each second well is of substantially square transverse cross-section.

In another embodiment of the invention the sample accommodating portion of each second well is adapted for carrying out a viscosity analysis of the sample.

In another embodiment of the invention the sample accommodating portion of each second well is adapted for accommodating a ball of magnetically responsive material therein and for facilitating movement of the ball therein in response to an applied magnetic field. Preferably, the sample accommodating portion of each second well comprises a base of circular shape and a side wall extending around and upwardly from the base. Ideally, the lower side wall of each second well comprises a cylindrical side wall. Advantageously, the sample accommodating portion of each second well defines an annular channel for guiding the ball around the base of the sample holding portion. Ideally, the annular channel of the sample accommodating portion of each second well is defined between the side wall of the sample accommodating portion and a projection extending upwardly from the base spaced apart from the side wall. Preferably, the projection extending upwardly from the base of the sample accommodating portion of each second well tapers upwardly from the base. Advantageously, the projection extending upwardly from the base of the sample accommodating portion of each second well is of conical shape.

In one embodiment of the invention each second well is adapted for holding a sample during an optical analysis thereof.

In another embodiment of the invention a portion of the sample accommodating portion of each second well is formed by respective lower portions of two spaced apart side walls, the lower portions of which extend parallel to each other.

Advantageously, the open mouth of each second well is located adjacent the plate.

Preferably, each second well extends downwardly from the plate.

In one embodiment of the invention a plurality of holding wells are provided, the holding wells being arranged in spaced apart columns, each column comprising a plurality of holding wells. Preferably, the columns of the holding wells extend parallel to each other. Advantageously, the holding wells of the respective columns are aligned to form a plurality of parallel rows thereof.

In another embodiment of the invention a plurality of analysis wells are provided, the analysis wells being located in a plurality of spaced apart columns, each column comprising a plurality of analysis wells, and the columns of holding wells and analysis wells being arranged alternately on the plate. Preferably, the analysis wells are aligned in the respective columns thereof to form a plurality of rows of the analysis wells. Advantageously, the analysis wells in each column thereof are alternately arranged as first wells and second wells. Ideally, the analysis wells of each row of analysis wells are of one of the first well type and the second well type. In one embodiment of the invention each holding well and each analysis well is adapted for holding a liquid sample.

Additionally, the invention provides a method for preparing a sample for analysis, the method comprising transferring the sample into a holding well of a well plate, and transferring a measured quantity of the sample from the holding well to an analysis well of the well plate for analysis therein.

In one embodiment of the invention the sample is mixed with another constituent in the holding well prior to being transferred to the analysis well.

In another embodiment of the invention the sample is transferred to the holding well from another holding well of the well plate prior to being mixed with the constituent.

Preferably, the sample is mixed with a reagent in the holding well. Advantageously, two accurately measured samples are transferred from the holding well to respective ones of first and second wells of the analysis wells. Ideally, the sample in the first well is analysed by an optical analysis method, and the sample in the second well is analysed by a mechanical analysis method.

In one embodiment of the invention the sample is a liquid sample.

In another embodiment of the invention the sample is a sample of bodily fluid.

The well plate according to the invention has many advantages. The well plate according to the invention facilitates pipetting of samples of relatively accurate sample size into the analysis wells, and additionally, facilitates mixing of samples with a reagent or other substance. Furthermore, the well plate according to the invention facilitates the provision of a sample of relatively accurate sample size which in turn can be mixed with a reagent or other substance.

By virtue of the fact that the well plate comprises holding wells, samples of relatively inaccurate size may be pipetted initially into the holding wells, and then subsequently pipetted from the holding wells to appropriate ones of the first or second analysis wells, or both by relatively accurate pipetting. Accurate pipetting of samples from each holding well to the analysis well or wells is achieved by virtue of the fact that the sample from the holding well is sampled at atmospheric pressure. The provision of each holding well with a hollow interior region which terminates in a downwardly tapering portion facilitates pipetting of samples therefrom due to the fact that the liquid level in the holding well for a sample of given size is higher than would be the case if the holding well terminated in a relatively flat or planar base.

A further advantage of the invention is achieved where it is desired to mix a sample with a reagent, in that the sample may be mixed in one of the holding wells with the reagent prior to being transferred to an appropriate one of the first and second analysis wells or both. Additionally, if it is desired to mix a sample of relatively accurate size with a reagent, an accurate sample may be pipetted from one holding well to another, and the accurate sample may then be mixed with the reagent in the holding well into which it has been transferred, before a sample of the mixed sample and reagent is pipetted into an appropriate one of the first and second analysis wells or into both a first and a second analysis well. A further advantage of the invention is that two or more reagents could be mixed in one of the holding wells prior to being transferred to another one of the holding wells for mixing with a sample.

BRIEF DESCRIPTION OF THE DRAWINGS

The invention will be more clearly understood from the following description of a preferred embodiment thereof, which is given by way of example only, with reference to the accompanying drawings, in which:

FIG. 3 is a transverse cross-sectional side elevational view of a detail of the well plate of FIG. 1 on the line II-II of FIG. 1, FIG. 4 is an enlarged transverse cross-sectional end elevational view on the line II-II of another detail of the well plate of FIG. 1, FIG. 5 is a transverse cross-sectional side elevational view of the detail of FIG. 4 of the well plate of FIG. 1 on the line IV-IV of FIG. 1, FIG. 6 is a transverse cross-sectional end elevational view of another detail of the well plate of FIG. 1 on the line II-II of FIG. 1, and FIG. 7 is a transverse cross-sectional side elevational view of the detail of FIG. 5 of the well plate of FIG. 1 on the line VII-VII of FIG. 1.

DETAILED DESCRIPTION OF THE INVENTION

Figure 1:
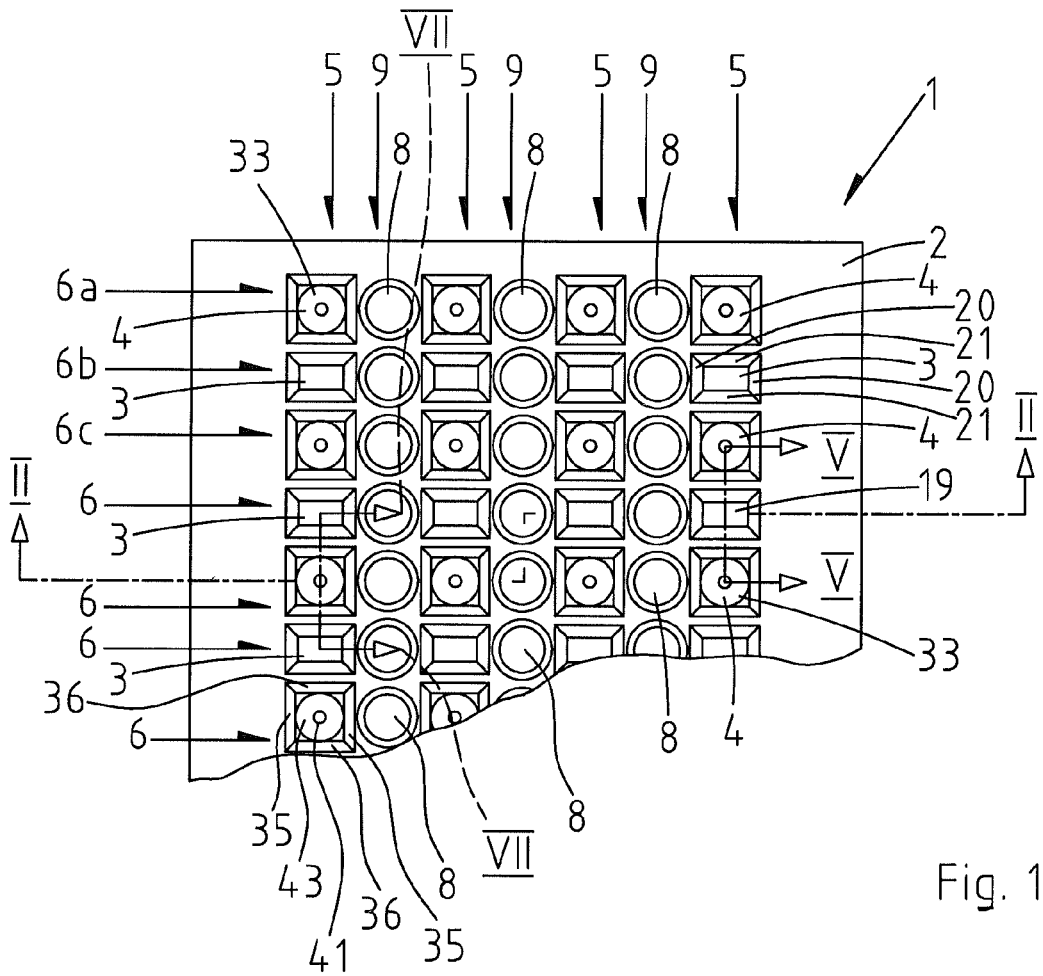
FIG. 1 is a top plan view of a portion of a well plate according to the invention.

Referring to the drawings, there is illustrated a well plate according to the invention, indicated generally by the reference numeral 1, for holding a liquid sample, for example, a sample of bodily fluid, such as blood, blood plasma, urine and the like during analysis thereof in an analytical apparatus (not shown). The analytical apparatus does not form part of the invention, and will not be described, however, such analytical apparatus will be well known to those skilled in the art. The analytical apparatus may be of the type which is suitable for carrying out an optical analysis or a mechanical analysis of the liquid sample, or, and more typically, it may be of the type which is capable of carrying out both an optical and a mechanical analysis of the liquid sample. In this embodiment of the invention the well plate 1 is suitable for use in a range of analytical apparatus sold under the trade name AMAX DESTINY by Trinity Biotech PLC of Ireland.

The well plate 1 comprises a plate 2, which in this embodiment of the invention is of a transparent semi-rigid plastics material. A plurality of analysis wells, in this embodiment of the invention first wells 3 and second wells 4 for holding the liquid samples during analysis thereof extend downwardly from the plate 2, and are arranged in a plurality of columns 5 and rows 6 as will be described below. The first wells 3 are adapted for facilitating the carrying out an optical analysis on a sample placed therein, while the second wells 4 are adapted for facilitating the carrying out a mechanical analysis on a sample placed therein, as will be described below. A plurality of holding wells 8 for holding samples prior to being transferred to an appropriate one or ones of the first and second wells also extend downwardly from the plate 2. The holding wells 8 are arranged in columns 9 which are alternately located with the columns 5 of the first and second wells 3 and 4, and respective ones of the holding wells 8 are arranged and aligned with the rows 6 of the first and second wells 3 and 4.

Typically, a liquid sample is pipetted from a vial or other such container into an appropriate one of the holding wells 8, and then an accurate sample of the liquid sample in the holding well 8 is accurately pipetted from the holding well 8 into one or more of the first and second wells 3 and 4, so that the samples pipetted into the first and second wells 3 and 4 are of accurate size. Additionally, if desired, the liquid sample may be mixed with a reagent in the holding well 8, or a more accurate sample size may be pipetted from the holding well into another one of the holding wells 8, and the reagent could then be mixed with the more accurate sample in the holding well 8 prior to a sample of the mixed sample and reagent being transferred into the appropriate one or ones of the first and/or second wells 3 and 4.

Referring now in particular to FIG. 3, each holding well 8 comprises an upper cylindrical side wall 10 which extends downwardly from the plate 2 and terminates in a lower conical side wall 12, which in turn terminates in a lower apex 14. The cylindrical side wall 10 and the conical side wall 12 together define a hollow interior region 15 for holding the liquid sample, and the cylindrical side wall 10 defines an upwardly facing open mouth 16 for accommodating the sample into the hollow interior region 15. The conical side wall 12 results in the hollow interior region 15 terminating in a downwardly tapering lower portion 17 which results in the level of the sample in the hollow interior region 15 and in the tapering portion 17 being maintained at a higher level than would otherwise be the case if the hollow interior region terminated in a flat base. The tapering portion 17 also facilitates more even distribution of constituents being mixed in the holding wells 8.

Each first well 3 comprises a planar base 19 of rectangular shape and a pair of spaced apart side walls 20 which extend upwardly from the base 19 to the plate 2 and which are joined by a pair of spaced apart end walls 21, which also extend upwardly from the base 19 to the plate 2. The base 19, the side walls 20 and the end walls 21 of each first well 3 define a hollow interior region 23 of rectangular transverse cross-section in plan view for receiving the liquid sample, and the side and end walls 20 and 21 define an open mouth 25 of rectangular shape for accommodating the liquid sample into the hollow interior region 23. The side and end walls 20 and 21 are polished to accommodate the transmission of light therethrough for facilitating optical analysis of the sample in each first well 3.

Referring now in particular to FIGS. 4 and 5, lower portions 27 of the side walls 20 extend upwardly from the base 19 parallel to each other and meet upper portions 29 of the side walls 20 at 31. Lower portions 28 of the end walls 21 also extend upwardly from the base 19 parallel to each other, and meet upper portions 30 of the end walls 21 at 32. The lower portions 27 of the side walls 20 and the lower portions 28 of the end walls 21 along with the base 19 of each first well 3 form a sample accommodating portion 26 of rectangular transverse cross-section in plan view for the sample. The upper portions 29 of the respective side walls 20 of each first well 3 extend upwardly from the corresponding lower portions 27 thereof at 31 to the plate 2 and diverge upwardly outwardly from each other to the open mouth 25. The upper portions 30 of the respective end walls 21 extend upwardly from the corresponding lower portions 28 thereof at 32 to the plate 2, and diverge upwardly outwardly from each other to the open mouth 25. The upper portions 29 and 30 of the side and end walls 20 and 21, respectively, diverge upwardly outwardly for accommodating the sample into the sample accommodating portion 26. The lower portions 27 and 28 of the side and end walls 20 and 21, respectively, are parallel to each other for facilitating optical analysis of the sample in the sample accommodating portion 26. By providing the respective lower portions 27 and 28 parallel to each other, light directed perpendicularly to any one of the lower portions 27 and 28 of the side and end walls 20 and 21 passes into the sample unrefracted.

Referring now in particular to FIGS. 6 and 7, each second well 4 comprises a base 33 of circular shape in plan view. A lower cylindrical side wall 34 extending around the base 33 extends upwardly to meet a pair of spaced apart side walls 35 and a pair of spaced apart end walls 36 at 37. The side and end walls 35 and 36 extend downwardly from the plate 2 and define an upwardly facing open mouth 39 of square cross-section to a hollow interior region 38 of the second well 4, which is defined by the base 33, the cylindrical side wall 34 and the side and end walls 35 and 36. Each side wall 35 of each second well 4 comprises an upper portion 50 and a lower portion 51. Each end wall 36 of each second well 4 comprises an upper portion 53 and a lower portion 54. The upper and lower portions 50 and 51 of each side wall 35 meet at 55, while the upper and lower portions 53 and 54 of the end walls 36 meet at 56. The lower portions 51 of the side walls 35 of each second well 4 are parallel to each other and extend upwardly from the lower cylindrical side wall 34 at 37 to the corresponding upper portions 50 of the side walls 35 at 55. The lower portions 54 of the end walls 36 of each second well 4 extend upwardly parallel to each other from the lower cylindrical side wall 34 at 37 to the corresponding upper portions 53 of the end walls 36 at 56. The lower portions 51 and 54 of the side and end walls 35 and 36, respectively, of each second well 4 together with the lower cylindrical side wall 34 and the base 33 define a sample accommodating portion 40 of the second well 4. The upper portions 50 of the side walls 35 of each second well 4 diverge upwardly outwardly from the corresponding lower portions 51 at 55 to the plate 2 to define with the upper portions 53 of the corresponding end walls 36 the open mouth 39. The upper portions 53 of the end walls 36 of each second well 4 also diverge upwardly outwardly from the corresponding lower portions 54 at 56 to the plate 2 adjacent the open mouth 39. The diverging upper portions 50 and 53 of the side walls 35 and 36, respectively, of each second well 4 accommodate the sample into the sample accommodating portion 40.

Figure 2:
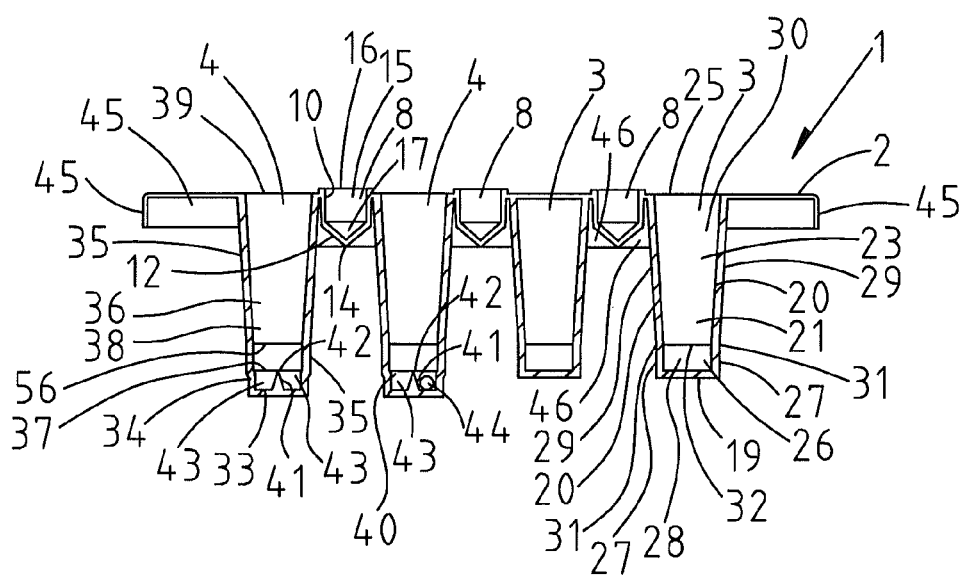
FIG. 2 is a transverse cross-sectional end elevational view of the well plate of FIG. 1 on the line II-II of FIG. 1.

A projection 41 of conical shape terminating in an upper apex 42 extends upwardly from the centre of the base 33 of each second well 4, and defines with the lower cylindrical side wall 34 an annular channel 43 for accommodating and guiding a ball 44 through a circular annular path around the base 33 within the sample for facilitating a determination of the viscosity of the sample. The ball 44 illustrated in the channel 43 in one of the second wells 4 illustrated in FIG. 2, and in FIG. 6 is of steel, and thus is magnetically responsive, and is propelled around the annular channel 43 by an externally applied magnetic field which is applied by the analytical apparatus in which the well plate 1 is placed for carrying out the analysis of the sample. The ball 44 does not form part of the invention. The lower cylindrical side wall 34, the upper side wall 35 and the upper end wall 36 are polished for also facilitating optical analysis of the sample in the second wells 4, if desired. Additionally, by virtue of the fact that the lower portions 51 and 54 of the respective side and end walls 35 and 36 of each second well 4 are parallel to each other also facilitates optical analysis of a sample in the sample accommodating portion 40. By providing the respective lower portions 51 and 54 parallel to each other, light directed perpendicularly to any one of the lower portions 51 and 54 passes into the sample in the sample accommodating portion 40 unrefracted.

The first and second wells 3 and 4 are alternately located along each column 5 of first and second wells 3 and 4. Each row 6 comprises only ones of first and second wells 3 and 4 of the same type. For example, the first of the rows 6a comprise second wells 4 only, while the second row 6b comprises first wells 3 only, and the third row 6c comprises second wells 4 only, and so on. However, each row 6 of first wells 3 and second wells 4 also comprises holding wells 8, which are located alternately with the corresponding ones of the first wells 3 and the second wells 4.

A downwardly extending reinforcing lip 45 extends downwardly and around the plate 2 for strengthening the plate 2. A plurality of spaced apart webs 46 extend downwardly from the plate 2 between the holding wells 8 and the first wells 3, and between the holding wells 8 and the second wells 4 in the respective rows 6.

In this embodiment of the invention the well plate 1 is of injection moulded plastics material, and the first and second wells 3 and 4 and the holding wells 8 are integrally injection moulded with the plate 2.

In use, the well plate 1 is inserted in an analytical apparatus, and a first pipetting mechanism also associated with the analytical apparatus sequentially pipettes liquid samples to be analysed from vials containing the samples which are also located in the analytical apparatus into the holding wells 8. When it is desired to subject a liquid sample to both optical and mechanical analysis, two accurately sized samples are sequentially pipetted from the appropriate holding well 8 by a second pipetting mechanism, also associated with the analytical apparatus to adjacent ones of the first and second wells 3 and 4, although in certain cases the sample or samples may be transferred from the holding well 8 to one or each of the first and second wells 3 and 4 by the first pipetting mechanism. The liquid samples in the first and second wells 3 and 4 are then subjected to respective optical and mechanical analysis in the analytical apparatus. If the samples are blood or blood plasma samples, the samples may be analysed for determining a characteristic of the sample, in order to, for example, make a diagnosis of a condition of a subject.

When it is desired to carry out only one of an optical and mechanical analysis, an accurately sized sample is pipetted from the holding well 8 into an appropriate one of the first and second wells 3 and 4, or two accurately sized samples may be pipetted from the holding well 8 into two adjacent appropriate ones of the first and second wells 3 and 4.

However, if desired, both mechanical and optical analysis of a sample may be carried out in any one of the second wells 4.

Should it be desired to mix a liquid sample with another constituent, for example, a reagent prior to analysis, the sample pipetted into the holding well 8 is mixed in the holding well 8 with the constituent or reagent, and one or more relatively accurate samples of the mixed sample and constituent or reagent are pipetted from the holding well 8 to one or more of the first and/or second wells 3 and 4 as desired. The samples in the first well 3 and/or the second well 4 are then subjected to the appropriate one of optical and mechanical analysis.

Should it be desired to mix a relatively accurately sized sample with another constituent or a reagent, a relatively accurately sized sample is pipetted from the holding well 8, into which the sample had been initially pipetted from one of the vials by the first pipetting mechanism, into another holding well 8 by the second pipetting mechanism, and the relatively accurately sized sample is mixed in the holding well 8 with the constituent or reagent and subsequently transferred to one or more of the first and second wells 3 and 4. Should it be desired to mix two or more constituents, such as reagents, to a sample, the two or more constituents may be mixed in one of the holding wells prior to being transferred to another one of the holding wells for mixing with the sample.

The actual analysis which is carried out by the analytical apparatus will depend on the samples and the characteristics of the samples which are to be determined or monitored, and will also depend on the material sampled.

While the well plate has been described as comprising analysis wells which are suitable for both optical and mechanical analysis, in certain cases, it is envisaged that the analysis wells may be all of one type, for example, may all be suitable for only one of optical or mechanical analysis. It will also be appreciated that while the first and second wells and the holding wells have been described as being located in the plate of the well plate in rows and columns, in certain cases, it is envisaged that the plate of the well plate may be provided as a single elongated strip which would comprise a plurality of the wells arranged in a single column extending longitudinally along the strip plate. In which case, it is envisaged that the holding wells and the analysis wells would be alternately arranged along the column, and where the well plate comprised both first and second wells, the first and second analysis wells would be arranged so that the first and second analysis wells would be alternately arranged with the holding wells.

While the well plate has been described as being of a plastics material and formed by injection moulding, the well plate may be of any other suitable material, and may be formed by any other suitable process.

While the samples have been described as being transferred by pipetting, any other suitable means of transferring the samples may be used.

While the side and end walls of the second wells have been described as being polished, while this is advantageous, in that it permits the second wells to be used for both mechanical and optical analysis, it is not essential. It is also envisaged in certain cases that the base of the second wells may also be polished for facilitating optical analysis. Needless to say, the second wells may be provided to be suitable for mechanical analysis only.

While the side and end walls of the first wells have been described as being polished, in certain cases, it is envisaged that only the side walls would be polished, or only the end walls would be polished. It is also envisaged in certain cases that only a part of the side and/or end walls would be polished, and it is also envisaged that in certain cases the base of the first wells may be polished.

While the well plate has been described as being suitable for a particular range of analytical apparatus, it will be readily apparent to those skilled in the art that the well plate may be used in any other analytical apparatus, and may be readily adapted for use in other analytical apparatus if required.

The invention claimed is:

1. A method for preparing a sample for analysis on a well plate comprising a plurality of analysis wells, at least one of the analysis wells being of a first type, and at least one of the analysis wells being of a second type, the at least one well of the second type defining a hollow interior region extending downwardly from an open mouth for accommodating the sample into the hollow interior region, and terminating in a sample accommodating portion, the sample accommodating portion having a base and defining an annular channel extending around the base for guiding a ball of a magnetically responsive material around the base in response to an applied magnetic field for carrying out a viscosity analysis of the sample, the method comprising:
   transferring the sample into a holding well of the well plate, and
   transferring a measured quantity of the sample from the holding well to an analysis well of the second type for a viscosity analysis therein.

2. A method as claimed in claim 1 in which the sample is mixed with another constituent in the holding well prior to being transferred to the analysis well.

3. A method as claimed in claim 2 in which the sample is transferred to the holding well from another holding well of the well plate prior to being mixed with the constituent.

4. A method as claimed in claim 1 in which the sample is mixed with a reagent in the holding well.

5. A method as claimed in claim 1 in which respective measured quantities of the sample are transferred from one of the holding wells to one of the analysis wells of the first type, and to the one of the analysis wells of the second type.

6. A method as claimed in claim 5 in which the sample in the analysis well of the first type is subjected to an optical analysis.

7. A method as claimed in claim 5 in which each well of the first type defines a hollow interior region extending downwardly from an open mouth for accommodating the sample into the hollow interior region, and terminating in a sample accommodating portion for holding the sample during analysis thereof, the sample accommodating portion comprising a planar base and a pair of spaced apart parallel side walls extending upwardly from the base, and a pair of spaced apart end walls extending upwardly from the base joining the side walls.

8. A method as claimed in claim 7 in which the end walls of the sample accommodating portion of each well of the first type extend parallel to each other.

9. A method as claimed in claim 7 in which the hollow interior region defined by each well of the first type tapers downwardly from the open mouth thereof to the sample accommodating portion.

10. A method as claimed in claim 9 in which the tapering portion of the hollow interior region of each well of the first type is formed by a pair of spaced apart side walls diverging upwardly from each other from the side walls of the sample accommodating portion, joined by a pair of spaced apart end walls diverging upwardly from each other from the end walls of the sample accommodating portion.

11. A method as claimed in claim 1 in which the base of the sample accommodating portion of each well of the second type comprises a base of circular shape and a lower side wall extending around and upwardly from the base.

12. A method as claimed in claim 1 in which the annular channel of the sample accommodating portion of each well of the second type is defined between the side wall of the sample accommodating portion and a projection extending upwardly into the sample accommodating portion from the base spaced apart from the lower side wall.

13. A method as claimed in claim 1 in which each well of the second type is adapted for holding a sample during an optical analysis thereof.

14. A method as claimed in claim 1 in which the sample is a liquid sample.

15. A method as claimed in claim 1 in which the sample is a sample of bodily fluid.

\* \* \* \* \*